United States Patent [19]

Mormile

[11] Patent Number: 4,835,227

[45] Date of Patent: May 30, 1989

[54] BLOCKED ACID CATALYSTS

[75] Inventor: Patrick J. Mormile, Wilbraham, Mass.

[73] Assignee: Monsanto Company, St. Louis, Mo.

[21] Appl. No.: 92,492

[22] Filed: Sep. 3, 1987

[51] Int. Cl.$^4$ .............................................. C08L 61/20
[52] U.S. Cl. ............................... 525/509; 260/505 R; 260/505 C; 502/159; 502/167; 502/168; 528/254; 525/162; 525/163; 525/428; 525/443; 525/456
[58] Field of Search ............... 525/509, 162, 163, 428, 525/443, 456; 528/250, 254, 391, 421; 260/505 R; 502/159, 167, 168

[56] References Cited

U.S. PATENT DOCUMENTS

| | | | |
|---|---|---|---|
| 4,192,826 | 3/1980 | Beresniewicz et al. | 525/425 |
| 4,200,729 | 4/1980 | Calbo | 528/254 X |
| 4,291,137 | 9/1981 | Nakate et al. | 525/162 |
| 4,582,894 | 4/1986 | Pfohl | 528/250 |

*Primary Examiner*—Theodore E. Pertilla
*Attorney, Agent, or Firm*—R. Bruce Blance; William J. Farrington

[57] ABSTRACT

Sulfonic acids blocked by reaction with glycidamides. The blocked acids are used as catalysts for resin curing systems and provide viscosity stability and pot life without significant decrease in catalytic activity in comparison with the corresponding free sulfonic acids.

7 Claims, No Drawings

BLOCKED ACID CATALYSTS

This invention relates to blocked acid catalysts and more particularly to blocked sulfonic acid catalysts.

Blocked acid catalysts are used in acid curing resin systems such as amino resins, melamine resins, urea-formaldehyde resins, phenol-formaldehyde resins and mixtures of such resins with alkyd, polyester or acrylic resins. Further acid-curable resins are methylol compounds, methylol ethers of polycarboxylic acid imides, for example derivatives of polyacrylic or methacrylic acid urethane alkyds and resins containing carboxylic acid esters of N-methylolimides. The acid curing catalysts used are mainly organic acids including, for example, sulfonic acids. Since these acids result in a fairly rapid curing at temperatures as low as room temperature, they are not added to the resin until shortly before the application of the latter. In order, therefore, to make one-component systems possible, the use of masked or blocked curing catalysts from which the acid is released at elevated temperature, has already been suggested. Example of these are amine salts of aromatic sulfonic acids, such as dimethyloxazolidine salts. These have the disadvantage that they result in a slow curing during storage to an unacceptable degree. In addition, problems of odor arise with these products. Also, resins cured with such blocked catalysts are found to be deficient in humidity resistance. Other examples of blocked catalysts are sulfonic acid adducts of conventional epoxy resins such as the glycidyl ethers of bisphenols and oligomers of such glycidyl ethers suggested in U.S. Pat. No. 4,192,826. These have the disadvantage that they require high temperatures for unblocking of the acid with the result that when they are used to cure resin systems at concentrations which do not cause excessive decrease in humidity resistance of the resin systems, they do not provide adequate cure at conventional baking temperatures.

According to the present invention, there is provided a blocked acid catalyst which can be used in acid curing resin systems. The blocked catalysts comprise the reaction product of a sulfonic acid and a glycidamide. Such products advantageously comprise at least one group per molecule represented by the formula:

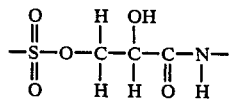

Any sulfonic acid containing up to four sulfonic acid units per molecule may be used to form the present composition. Representative sulfonic acids are compounds of the formula:

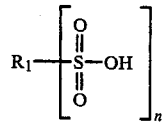

in which n is in the range of 1 to 4, and if n is 1, $R_1$ is for example $C_1$ to $C_{18}$ alkyl, phenyl which is unsubstituted or substituted for example with halogen, $C_1$–$C_{12}$ alkyl, $C_1$–$C_4$ alkoxy, $C_1$–$C_4$ alkyl CONH, phenyl —CONH, —$NO_2$ or benzoyl, naphthyl which is unsubstituted or substituted for example with halogen, $C_1$–$C_{12}$ alkyl or $C_1$–$C_4$ alkoxy, $C_5$–$C_6$ cycloalkyl, $C_7$–$C_9$ aralkyl, camphoryl, —$CF_3$, —$CCl_3$, —F or $NH_2$, and if n=2, $R_1$ is for example $-(CH_2)_m$ where m is 2 to 8, or $R_1$ is for example phylene or naphthylene which are unsubstituted or substituted for example with $C_1$–$C_{12}$ alkyl, and if n=3, $R_1$ is for example a trivalent aliphatic radical ($C_pH_{2p-1}$) where p is 2 to 8, or $R_1$ is for example a trivalent $C_6$–$C_{10}$ aromatic radical which is unsubstituted or substituted for example with $C_1$–$C_{12}$ alkyl, and if n=4, $R_1$ is for example a tetravalent aliphatic radical ($C_pH_{2p-2}$) where p is 2 to 8, or $R_4$ is for example a tetravalent $C_6$–$C_{10}$ aromatic radical which is unsubstituted or substituted for example with $C_1$–$C_{12}$ alkyl.

Preferred sulfonic acids are aromatic sulfonic acids and include benzene sulfonic acid, benzenedisulfonic acid, o- and p- toluenesulfonic acid, toluene disulfonic acid, $C_2$–$C_{18}$ alkylbenzenesulfonic acids, $C_2$–$C_{18}$ alkylbenzenediculfonic acids, o- and p-dodecylbenzene-sulfonic acid, naphthylenesulfonic acid, and $C_1$–$C_{18}$ alkylnaphthalene sulfonic acids naphthalenedisulfonic acid and $C_1$–$C_{18}$ alkylnaphthalenedisulfonic acids.

Any glycidamide containing up to four glycidamide groups per molecule can be reacted with the sulfonic acid to form the blocked acids of the present invention. Reaction ratios are preferably selected to limit the number of blocked acid units to an average of 6 per molecule of blocked acid catalyst. When the valence of the sulfonic acid is greater than one, a monoglycidamide is preferably used as the blocking agent. Similarly when the glycidamide contains more than one glycidamide group per molecule, a monovalent sulfonic acid is preferably selected for reaction. Representative glycidamides include for example glycidamide, N-alkylglycidamides in which alkyl is $C_1$–$C_{12}$, N-aryl-glycidamides in which aryl is $C_6$–$C_{10}$, N-alkylene diglycidamides in which alkylene is $C_1$–$C_{12}$, N-arylene diglycidamides in which arylene is $C_6$–$C_{10}$, and mono- and poly-glycidamide derivatives of amino compounds such as urea, glycouril and aminotriazines for example melamine and benzoguanamine, in which the glycidamide is linked to the amino compound by a methylene group. Such glycidamidomethyl, amino compounds include those disclosed in U.S. Pat. No. 4,582,894. They offer the opportunity for incorporation into resin systems upon cure, not only through their epoxy groups but also through alkoxymethyl substituents of the amino compounds.

The blocked acid catalyst is prepared by mixing the two components together in bulk or in solution in proportions such that there is 0.1 to 1 sulfonic acid group per glycidamido group, and the resultant mixture is allowed to react for 20 to 60 minutes at a temperature in the range of 20° to 150° C., preferably 20° to 80° C. The order of addition of the reactants is immaterial; however it is preferred to add the sulfonic acid to the glycidamide at a temperature which maintains the reactants in liquid form.

The blocked acid catalyst can be used to catalize the cure of any acid-curable resin system. For example it can be used to catalyze the cure of resins containing hydroxy, carboxy, or amide groups by amino resins such as amino triazine formaldehyde resins and urea-formaldehyde resins. Suitable amino resins are prepared for example by the condensation of at least one aldehyde with at least one of urea, N,N'-ethyleneurea, dicyandiamide, glycouril and aminotriazines such as melamines and guanamines such as guanamine and acylguanamines in which the aryl group contains from 2 to 7 carbon atoms, such as aceto and benzoguanamine. Among the aldehydes that are suitable are formaldehyde, revertable polymers thereof such as paraformaldehyde, acetaldehyde, crotonaldehyde, and acrolein. Preferred are formaldehyde and revertable polymers thereof. The amino-resins are preferably alkylated with at least one and up to to six alkanyl molecules containing 1 to 8 carbon atoms. The alkanols can be straight chain, branched or cyclic or mixtures thereof. Among preferred members of this class are the methylated melamine-formaldehyde resins such as hexamethoxymethylmelamine and mixed peralkoxy derivatives such as trimethoxymethyltributoxymethylmelamine. These crosslinking agents have substantially 100% non-volatile content.

The amino resin crosslinking agent is present in an amount of 10–70 parts by weight of the curable resin system and preferably 20–50 parts.

The resin containing hydroxy, carboxy or primary or secondary amide groups curable by means of the amino resin may be a vinyl addition polymer formed by interpolymerization of acid, hydroxy, or amide monomer and non-functional vinyl monomers such as acrylic monomers, styrene monomers, vinyl esters and acrylonitriles and the like. The acid monomer may be selected from the group consisting of acrylic acid, methacrylic acid, crotonic acid, maleic acid, fumaric acid, itaconic acid and monohydrocarbyl esters of monounsaturated polyacids such as the alkyl hydrogen maleates and alkyl hydrogen fumarates for example methyl hydrogen maleate, butyl hydrogen maleate, octyl hydrogen fumarate and the like. The hydroxy monomer may be selected from the group consisting of hydroxyhydrocarbyl esters of monounsaturated mono- and poly-acids such as 2-hydroxyethyl acrylate, 2-hydroxyethyl methacrylate, 2-hydroxypropyl acrylate, 3-hydroxypropyl methacrylate, bis(2-hydroxyethyl)-maleate, bis(3-hydroxypropyl) fumarate and the like. The amide monomer may be selected from the group consisting of acrylamide, methacrylamide, and N-hydrocarbylacrylamides such as N-methylacrylamide and N-ethylacrylamide and the like. Also the resin can be selected from conventional polyester, polyamide, polyether-urethane and polyester-urethane condensation products. The polyester condensation products include conventional oil-free and oil modified alkyd resins and oil-free and oil modified urethanealkyds. In general the condensation polymers possess a functionality of at least two provided by carboxy, and/or hydroxy, and/or primary or secondary amide. The resin can also be a polyhydric alcohol such as a styrene-allyl alcohol copolymer or a polyether polyol.

In general, the acid curable resin has a number average molecular weight of at least about 500 and is preferably in the range of about 1000 to 20000. The functionality of the resin is at least 2 and is generally present to provide from about 1 equivalent of functional group per 150 to 10000 units of molecular weight.

The blocked acid catalyst utilized in thermosetting compositions is present in sufficient amount to accelerate the cure of the compositions. A satisfactory amount is generally in the range of 0.001 to 0.02 equivalents of potentially available sulfonic acid when unblocking takes place per 100 parts of resin solids.

The compositions comprising reactive resin and amino crosslinking agent may also include solvents to provide a viscosity suitable for the method of application. Preferably the compositions contain no more than about 30 weight percent of solvent based on the weight of solvent and resins. The compositions may also include various conventional modifiers such as catalysts, accelerators, flow control agents, surface active agents, organic and inorganic pigments, inert fillers, inhibitors, stabilizers and plasticizers.

While solvent coating compositions have been selected as resin systems amenable to cure by means of the blocked acid catalysts of the present invention, other resin systems such as thermosetting molding compositions, laminating compositions, potting compounds and powder coating compositions can be cured by the blocked acid catalysts.

The following examples illustrate the invention but are not to be construed as limiting its scope. All quantities are on a weight basis unless otherwise indicated.

EXAMPLES 1–4 AND COMPARATIVE EXAMPLES 1–3

Preparation of Blocked Catalysts

The blocked catalysts are prepared by mixing at room temperature (24°–26° C.). The reaction that takes place between the acid and the blocking agent (either epoxy or amine) is mildly exothermic and proceeds quite readily.

EXAMPLE 1 p-Toluenesulfonic acid/Glycidamide 122.9 parts by weight of a 70% p-toluene-sulfonic acid solution supplied in Methanol by Jim Walters Resources is mixed with 282.6 parts by weight of methanol. This solution is then added to 167.5 parts by weight of a 26% glycidamide solution in Dowanol PM to give a homogeneous clear solution.

EXAMPLE 2 p-Toluenesulfonic acid/Glycidamidomethyl melamine 246.0 parts by weight of the 70% p-toluene-sulfonic acid solution of Example 1 is mixed with 100.0 grams of isopropanol. This solution is then added to 526.0 grams of a 60% solution on Dowanol PM of an epoxy product obtained by condensation of 1 mole of a methoxymethylmelamine sold by Monsanto under the tradename Resimene ® R-755, 2.75 moles of acrylamide, and 1 mole of pentanol, followed by epoxidization under basic conditions, using potassium hydroxide and hydrogen peroxide in the presence of acetonitrile. The epoxide equivalent weight of the epoxy product is 270–330. The viscosity at 25° C. is 150–400 cps. The number average molecular weight is 1200. The color is 3 max. (Gardner) at 25° C.

EXAMPLE 3

Dodecylbenzenesulfonic acid/Glycidamide 233.0 parts by weight of a 70% dodecylbenzenesulfonic acid solution supplied in isopropanol by American Cyanamid is mixed with 415.0 parts by weight of methanol. This solution is then added to 167.5 parts by weight of a 26% glycidamide solution of Example 1 till homogeneous and clear.

EXAMPLE 4

Dodecylbenzenesulfonic acid/glycidamidomethyl melamine 233.0 parts by weight of the 70% dodecylbenzenesulfonic acid solution used in Example 2 is mixed with 319.0 parts by weight of additional isopropanol. This solution is then added to 263.0 grams of the epoxy product used in Example 3 and mixed until clear and homogeneous.

COMPARATIVE EXAMPLE 1 p-Toluenesulfonic acid/bisphenol A epoxy resin 110.0 parts by weight of the 70% p-toluenesulfonic acid used in Example 1 is mixed with 203.0 parts by weight of additional methanol. This solution is then added to 200.0 parts by weight of Epon 815 resin, an epoxy resin supplied by Shell as a 100% active liquid. These two components are then mixed till homogeneous and clear. Epon 815 is an epichlorohydrin/bisphenol A reaction product which contains a reactive diluent (glycidyl ether type). It is supplied by Shell Chemical Company as a 100% active liquid material. The epoxide equivalent is 175-195. The viscosity at 25° C. is 5-7 poise. The average molecular weight is 330. The color is 5 max. (Gardner) at 25° C.

COMPARATIVE EXAMPLE 2

Dodecylbenzenesulfonic acid/bisphenol A epoxy resin 210.0 parts by weight of the 70% dodecylbenzene sulfonic acid solution used in Example 3 is mixed with 325.0 parts by weight of additional methanol. This solution is then added to 200.0 parts by weight of Epon 815 resin. These two components are then mixed till homogeneous and clear.

COMPARATIVE EXAMPLE 3

Dodecylbenzenesulfonic acid/Dimethyloxazolidine (DMO)

204.0 parts by weight of the 70% dodecylbenzene sulfonic acid solution of Example 3 is mixed with 233.5 grams of additonal Methanol. This solution is then added to 62.5 grams of a 78% dimethyloxazolidine solution in water, supplied by Angus Chemicals. These two components are then mixed till clear and homogeneous.

EXAMPLES 5-8 AND COMPARATIVE EXAMPLES 4-8

A Resin formulation was prepared by blending a 60 weight percent solution of a hydroxy functional acrylic resin of number average molecular weight 2000, weight average molecular weight 4000 and hydroxyl number 140 with a hexamethoxymethyl melamine resin sold by Monsanto Company under the registered trademark Resimene 755. The acrylic resin was a copolymer of hydromethyl acrylate, methyl acrylate, butyl acrylate and styrene. To individual samples of the blend, the blocked sulfonic acids of examples 1-4 were added. Resin blends containing sulfonic acids and blends containing acid catalysts blocked with conventional epoxy were also prepared for comparative tests. All p-toluenesulfonic acid systems provided 0.4 weight percent p-toluenesulfonic acid based on total resin present in the system and all dodecylbenzenesulfonic acid systems provided 0.8 weight percent acid when unblocking took place. The compositions of the blend samples are set forth in Table 1 and data for viscosity stability at 60° C. are set forth in Table 2 illustrating the fast gellation which occurs with unblocked catalyst (comparative examples 4,5) and the slow increase in viscosity with the blocked catalysts in which blocking is achieved by reaction with epoxy compounds.

TABLE 1

| | Resin Blends (parts by weight) | | | | | | | | |
|---|---|---|---|---|---|---|---|---|---|
| | Ex 5 | Ex 6 | Ex 7 | Ex 8 | Comp. Ex 4 | Comp. Ex 5 | Comp. Ex 6 | Comp. Ex 7 | Comp. Ex 8 |
| Acrylic Resin | 143 | 143 | 143 | 143 | 143 | 143 | 143 | 143 | 143 |
| Resimene 755 Resin | 53 | 53 | 53 | 53 | 53 | 53 | 53 | 53 | 53 |
| pTSA | — | — | — | — | .78 | — | — | — | — |
| DDBSA | — | — | — | — | — | 1.56 | — | — | — |
| Catalyst Ex 1 | 3.70 | — | — | — | — | — | — | — | — |
| Catalyst Ex 2 | — | 2.75 | — | — | — | — | — | — | — |
| Catalyst Ex 3 | — | — | 5.50 | — | — | — | — | — | — |
| Catalyst Ex 4 | — | — | — | 5.50 | — | — | — | — | — |
| Catalyst Comp. Ex 1 | — | — | — | — | — | — | 3.70 | — | — |
| Catalyst Comp. Ex 2 | — | — | — | — | — | — | — | 5.50 | — |
| No catalyst | — | — | — | — | — | — | — | — | — |
| Xylene | 25 | 25 | 25 | 25 | 25 | 25 | 25 | 25 | 25 | pTSA = p-toluenesulfonic acid  DDBSA = dodecylbenzenesulfonic acid

TABLE 2

| Viscosity Stability of Resin Blends at 60° C. | | | | | |
|---|---|---|---|---|---|
| | Viscosity, cps | | | | |
| | Initial | 1 week | 2 weeks | 3 weeks | 4 weeks |
| Example | | | | | |
| 5 | 70 | 290 | 1010 | 1710 | gelled |
| 6 | 70 | 280 | 900 | 1640 | gelled |
| 7 | 70 | 310 | 900 | 1540 | 4000 |
| 8 | 70 | 300 | 850 | 1520 | 3800 |
| Comparative Example | | | | | |
| 4 | 75 | 1920 | gelled | — | — |
| 5 | 75 | 1250 | gelled | — | — |
| 6 | 70 | 240 | 720 | 1250 | 3150 |
| 7 | 70 | 250 | 700 | 1200 | 3000 |

TABLE 2-continued

| Viscosity Stability of Resin Blends at 60° C. | | | | | |
|---|---|---|---|---|---|
| | Viscosity, cps | | | | |
| | Initial | 1 week | 2 weeks | 3 weeks | 4 weeks |
| 8 | 75 | 75 | 75 | 75 | 75 |

The resin blends were applied by drawdown to primed Bonderite 40 steel panels to provide a dry coating thickness of 1.5-2.0 mil (37-51 micron) and the coatings were cured for 30 minutes at 250° F. (121° C.) and tested for solvent resistance, pendulum hardness (Konig oscillator) and gloss retention (60° angle) under condensing humidity conditions at 100% relative humidity and at 38° C. for 240 hours and upon exposure under QUV conditions for 1000 hours under cycles of condensing humidity for 4 hours at 50° C. and UV exposure for 8 hours at 60° C. The data are presented in Table 3 and show that coatings cured with sulfonic acids blocked with glycidamides are equivalent in performance to coatings cured with free acid and are significantly superior to coatings cured with sulfonic acids blocked with conventional epoxy resins.

TABLE 3

| Evaluation of Coatings Prepared from Acid Catalyzed Resin Blends | | | | |
|---|---|---|---|---|
| | Solvent Resistance (MEK double rubs) | Pendulum Hardness (Konig oscill.) | Condensing Humidity Gloss Retention | QUV Gloss Retention |
| Example | | | | |
| 5 | 100+ | 111.8 | 91 | 86 |
| 6 | 100+ | 107.5 | 91 | 86 |
| 7 | 100+ | 109.9 | 90 | 85 |
| 8 | 100+ | 105 | 91 | 85 |
| Comparative Example | | | | |
| 4 | 100+ | 112 | 91 | 86 |
| 5 | 100+ | 110 | 90 | 85 |
| 6 | 50 (break) | 90.0 | 80 (sl w) | 70 (sl y) |
| 7 | 45 (break) | 89.1 | 81 (sl w) | 70 (sl y) | w-whitening
y-yellowing fonic acid, and the blocked acids of example 4 and comparative example 3 were added. The compositions of the blend samples are set forth in Table 4 and viscosity stability of the glycidamide blocked catalyst system.

TABLE 4

| Resin Blends (parts by weight) | | | | |
|---|---|---|---|---|
| | Ex. 9 | Comp. Ex 9 | Comp. Ex 10 | Comp. Ex 11 |
| Acrylic resin | 143 | 143 | 143 | 143 |
| Resimene 755 Resin | 53 | 53 | 53 | 53 |
| DDBSA | — | 1.56 | — | — |
| Catalyst Ex 4 | 5.50 | — | — | — |
| Catalyst Comp. Ex. 3 | — | — | 3.82 | — |
| No catalyst | — | — | — | — |
| Xylene | 25 | 25 | 25 | 25 |

TABLE 5

| Viscosity Stability of Resin Blends at 60° C. | | | | | | |
|---|---|---|---|---|---|---|
| | viscosity, cps. | | | | | |
| | initial | 4 days | 12 days | 18 days | 25 days | 31 days |
| Example 9 | 190 | 750 | 1560 | 2640 | 5000 | gelled |
| Comp Ex 9 | 220 | 1212 | gelled | — | — | — |
| Comp Ex 10 | 190 | 555 | 8600 | gelled | — | — |
| Comp Ex 11 | 190 | 300 | 300 | 300 | 320 | 320 |

The resin blends were applied by drawdown to primed Bonderite 40 steel panels to provide a dry coating thickness of 1.5-2.0 mil (37-51 micron) and the coatings were cured under a range of conditions (30 minutes at 210° F., 250° F. and 275° F., −99° C., 121° C. and 135° C.) and tested for solvent resistance, pendil hardness, Tukon hardness and gloss retention (60° angle) after 240 hours under condensing humidity conditions at 100% relative humidity and 38° C. and gloss retention upon exposure under QUV conditions for 750 hours (cycle time 4 hours of condensing humidity at 50° C., 8 hours UV exposure at 65° C.) and adhesion rating after 1700 hours. The data are presented in Table 6. They show that the glycidamide blocked catalyst provides a faster cure rate than amine blocked catalyst and superior coating properties.

TABLE 6

| | Cure Response of Resin Blends | | | | | | | | | | | |
|---|---|---|---|---|---|---|---|---|---|---|---|---|
| | Example 9 | | | Comp. Example 9 | | | Comp. Example 10 | | | Comp. Example 11 | | |
| | 210° F. | 250° F. | 275° F. | 210° F. | 250° F. | 275° F. | 210° F. | 250° F. | 275° F. | 210° F. | 250° F. | 275° F. |
| Solvent resistance, MEK double rubs | 64 (break) | 100 (no mar) | 100 (no mar) | 100 (mars badly) | 100 (no mar) | 100 (no mar) | 42 (break) | 100 (no mar) | 100 (no mar) | sticky (no cure) | sticky (no cure) | sticky (no cure) |
| Pencil hardness | B | H-2H | 2H | B | H-2H | 2H | B | H-2H | H-2H | — | — | — |
| Tukon hardness, kg/mm² | <1 | 9.1 | 10.3 | <1 | 9.5 | 10.7 | <1 | 8.9 | 10.1 | — | — | — |
| Gloss retention, initial/final (condensing humidity) | 85/80 | 86/85 | 85/84 | 83/82 | 85/85 | 86/83 | 83/71 (blushed) | 84/83 | 84/83 | — | — | — |
| Gloss retention, initial/final (QUV conditions) | — | 86/80 | — | — | 85/80 | — | — | 84/75 | — | — | — | — |
| Adhesion rating after 1700 hours QUV exposure | — | 10 | — | — | 10 | — | — | 9 | — | — | — | — |
| Coating resistivity (initial) megaohms. | — | 0.75 | — | — | 1.0 | — | — | 0.6 | — | — | — | — |

EXAMPLE 9 AND COMPARATIVE EXAMPLES 9-11

A series of resin formulations were prepared by blending with Resimene 755 melamine resin. To individual samples of the blend free dodecylbenzenesul-

I claim:
1. A composition of matter comprising the reaction product of a sulfonic acid and a glycidamide, wherein the ratio of sulfonic acid groups to glycidamide groups is in the range of 0.1:1 to 1:1.

2. The composition of claim 1 comprising at least one unit per molecule of reaction product represented by the formula

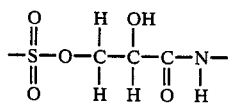

3. The composition of claim 1 wherein the sulfonic acid comprises from 1 to 4 sulfonic acid groups per molecule.

4. The composition of claim 1 wherein the sulfonic acid is an aromatic sulfonic acid.

5. The composition of claim 4 wherein the sulfonic acid is selected from the group consisting of benzenesulfonic acid, alkylbenzenesulfonic acid, benzene disulfonic acid, alkylbenzene disulfonic acid, naphthalene sulfonic acid, alkylnaphthalenesulfonic acid, naphthalene disulfonic acid, and alkylnaphthalene disulfonic acid in which alkyl is $C_1$ to $C_{18}$.

6. The composition of claim 1 wherein the glycidamide is selected from the group consisting of glycidamide and N-substituted glycidamides comprising from 1 to 4 glycidamido groups per molecule.

7. The composition of claim 6 wherein the glycidamide is a glycidamidomethyl substituted amino resin.

* * * * *